（12）United States Patent
Syms

(10) Patent No.: US 12,089,012 B2
(45) Date of Patent: Sep. 10, 2024

(54) AUDITORY FUNCTION SCREENING

(71) Applicant: Listen Up Hearing Technologies, LLC, Paradise Valley, AZ (US)

(72) Inventor: Mark James Syms, Paradise Valley, AZ (US)

(73) Assignee: Listen Up Hearing Technologies, LLC, Paradise Valley, AZ (US)

( * ) Notice: Subject to any disclaimer, the term of this patent is extended or adjusted under 35 U.S.C. 154(b) by 135 days.

(21) Appl. No.: 17/690,991

(22) Filed: Mar. 9, 2022

(65) Prior Publication Data

US 2023/0292070 A1 Sep. 14, 2023

(51) Int. Cl.
*H04R 29/00* (2006.01)
*H04R 3/04* (2006.01)
*H04R 5/033* (2006.01)
*H04R 5/04* (2006.01)

(52) U.S. Cl.
CPC ............. *H04R 29/001* (2013.01); *H04R 3/04* (2013.01); *H04R 5/033* (2013.01); *H04R 5/04* (2013.01); *H04R 2420/07* (2013.01)

(58) Field of Classification Search
CPC ........ H04R 29/001; H04R 3/04; H04R 5/033; H04R 5/04; H04R 2420/07
USPC .... 381/98, 60, 58, 23.1, 315, 317, 320, 312; 600/559; 73/585
See application file for complete search history.

(56) References Cited

U.S. PATENT DOCUMENTS

| | | | | |
|---|---|---|---|---|
| 3,970,785 A | * | 7/1976 | Meyer | A61B 5/121 73/585 |
| 9,571,949 B2 | * | 2/2017 | Rasmussen | A61B 5/123 |
| 10,130,287 B2 | | 11/2018 | Von Kraus et al. | |
| 2004/0204191 A1 | * | 10/2004 | Raviv | A61B 5/121 455/575.1 |
| 2009/0013787 A1 | | 1/2009 | Esnouf | |
| 2009/0156959 A1 | * | 6/2009 | Thornton | A61B 5/121 600/559 |
| 2013/0274628 A1 | * | 10/2013 | Fausti | A61B 5/123 600/559 |
| 2018/0098720 A1 | | 4/2018 | Raz et al. | |
| 2020/0345278 A1 | | 11/2020 | Mortensen | |

* cited by examiner

*Primary Examiner* — Vivian C Chin
*Assistant Examiner* — Con P Tran
(74) *Attorney, Agent, or Firm* — Knobbe Martens Olson & Bear, LLP

(57) ABSTRACT

An auditory function screening device includes a controller, a speaker, a microphone, an actuator, a display, a communication engine, and a memory. The speaker generates tones of each frequency of a set of test frequencies. The microphone detects ambient noise. The actuator initiates an auditory function screening test. The display displays an indication corresponding to a total number of generated tones. The communication engine communicates with an external computing device. The memory stores executable instructions that implement the auditory function screening test, which includes: detecting an ambient noise amplitude, determining a gain adjustment, generating a predetermined number of tones of each frequency of the set of test frequencies at a predetermined gain level based on the gain adjustment, presenting an indication corresponding to the total number of generated tones, and causing a use counter to be incremented.

24 Claims, 6 Drawing Sheets

AUDITORY FUNCTION SCREENING

TECHNICAL FIELD

This disclosure relates to the field of auditory function screening and systems and methods for remediating non-use of auditory function screening devices.

BACKGROUND

Complex hearing assessment devices are used to analyze and quantify auditory function. Highly trained clinicians or specialists use such devices to perform detailed auditory function testing. However, a portable, simple screening device would be useful to quickly identify individuals that may require further auditory function testing.

SUMMARY

Various techniques for proving auditory function screening, sometimes referred to as hearing screening, are described herein. Screening individuals for potential hearing loss does not provide a comprehensive assessment of auditory function. Instead, screening merely indicates whether hearing loss appears to have occurred, to some degree, and whether further testing may be indicated.

In some aspects, the techniques described herein relate to an auditory function screening device configured to screen a user (e.g., a patient, a subject, etc.) for possible hearing loss, including: a controller; a speaker coupled to the controller and configured to generate tones of each frequency of a set of test frequencies; a microphone coupled to the controller and configured to detect ambient noise in a testing environment; an actuator, coupled to the controller and configured to be activated to initiate an auditory function screening test; a display coupled to the controller and configured to display an indication corresponding to a total number of generated tones; a communication engine coupled to the controller and configured to communicate with an external computing device; and a memory coupled to the controller, the memory storing executable instructions that when executed by the controller cause the auditory function screening device to perform the auditory function screening test, the auditory function screening test including: detecting an ambient noise amplitude from the ambient noise in the testing environment; determining a gain adjustment based on the detected ambient noise amplitude; generating a predetermined number of tones of each frequency of the set of test frequencies at a predetermined gain level based on the gain adjustment; presenting an indication corresponding to the total number of generated tones; and causing a use counter to be incremented.

In some aspects, the techniques described herein relate to a system, wherein the controller includes a microprocessor or a microcontroller.

In some aspects, the techniques described herein relate to a system, wherein the display includes a screen or a light emitting diode.

In some aspects, the techniques described herein relate to a system, wherein the communication engine includes a radio configured to communicate according to an IEEE 802 wireless networking standard.

In some aspects, the techniques described herein relate to a system, wherein the memory is further configured to store data corresponding to the use counter.

In some aspects, the techniques described herein relate to a system, wherein the auditory function screening test includes determining the gain adjustment such that the auditory function screening test generates the tones at a gain of 25 dB, or at a variable or user-selectable gain, above the ambient noise amplitude.

In some aspects, the techniques described herein relate to a system, wherein the set of test frequencies includes 500 Hz, 1000 Hz, 2000 Hz, 4000 Hz, and 6000 Hz.

In some aspects, the techniques described herein relate to a system, wherein the auditory function screening test includes causing the use counter to be incremented by retrieving a use counter value from the memory, increasing the use counter value by one, and storing the increased use counter value in the memory.

In some aspects, the techniques described herein relate to a system, wherein the auditory function screening test includes causing the use counter to be incremented by proving an indication to a remote computing system that the auditory function screening test has been performed. In some aspects, the auditory function screening test includes causing the use counter to be reset or zeroed, such as, for example, by pressing a button or by removing a power supply (e.g., batteries).

In some aspects, the techniques described herein relate to a system, wherein the controller is further configured to perform active noise cancellation using the detected ambient noise.

In some aspects, the techniques described herein relate to a system, wherein the predetermined number of tones is the same for each frequency of the set of test frequencies.

In some aspects, the techniques described herein relate to a system, wherein the predetermined number of tones is different for at least two frequencies of the set of test frequencies.

In some aspects, the techniques described herein relate to a method of performing auditory function screening to screen a user for possible hearing loss, including: determining an ambient noise amplitude; determining a gain adjustment based on the detected ambient noise amplitude; generating a predetermined number of tones of each frequency of a set of test frequencies at a predetermined gain level based on the gain adjustment; presenting an indication corresponding to the predetermined number of tones; and causing a use counter to be incremented.

In some aspects, the techniques described herein relate to a method, further including communicating with an external computing device according to an IEEE 802 wireless networking standard.

In some aspects, the techniques described herein relate to a method, further including storing data corresponding to the use counter.

In some aspects, the techniques described herein relate to a method, further including determining the gain adjustment such that the tones are generated at a gain of 25 dB above the ambient noise amplitude.

In some aspects, the techniques described herein relate to a method, wherein the set of test frequencies includes 500 Hz, 1000 Hz, 2000 Hz, 4000 Hz, and 6000 Hz.

In some aspects, the techniques described herein relate to a method, further including causing the use counter to be incremented by retrieving a use counter value from a memory, increasing the use counter value by one, and storing the increased use counter value in the memory.

In some aspects, the techniques described herein relate to a method, further including causing the use counter to be incremented by proving an indication to a remote computing system that the auditory function screening test has been performed.

In some aspects, the techniques described herein relate to a method, further including detecting ambient noise and performing active noise cancellation using the detected ambient noise. In some aspects, a value, image, or indicator corresponding to the detected ambient noise is displayed or otherwise reported to the user. The detected ambient noise may correspond to ambient noise detected from an internal microphone, an external microphone, or both. The internal microphone may be positioned at an internal surface of an earphone configured to at least partially cover a user's ear. The external microphone may be positioned at an external surface of an earphone configured to at least partially cover a user's ear.

In some aspects, the techniques described herein relate to a method, wherein the predetermined number of tones is the same for each frequency of the set of test frequencies.

In some aspects, the techniques described herein relate to a system, wherein the predetermined number of tones is different for at least two frequencies of the set of test frequencies. In some aspects, the number of tones for each frequency is randomly generated. The number of tones may be any number, such as 1, 2, or 3. Such configuration prevents a patient from learning the system and predicting what the device will generate as a test pattern. Such randomization also enables retesting of the subject without informing the subject of the test pattern that will be administered during subsequent tests.

BRIEF DESCRIPTION OF DRAWINGS

Throughout the drawings, reference numbers may be re-used to indicate correspondence between referenced elements. The drawings are provided to illustrate example embodiments described herein and are not intended to limit the scope of the disclosure.

DETAILED DESCRIPTION OF ILLUSTRATIVE EMBODIMENTS

The present disclosure is directed to auditory function screening, including devices and methods for quickly determining whether an individual may have some degree of hearing loss and correct for ambient noise. The present disclosure is also directed to remediating non-use of auditory function screening devices, such as those described herein.

Hearing Screening Devices

Figure 1C:
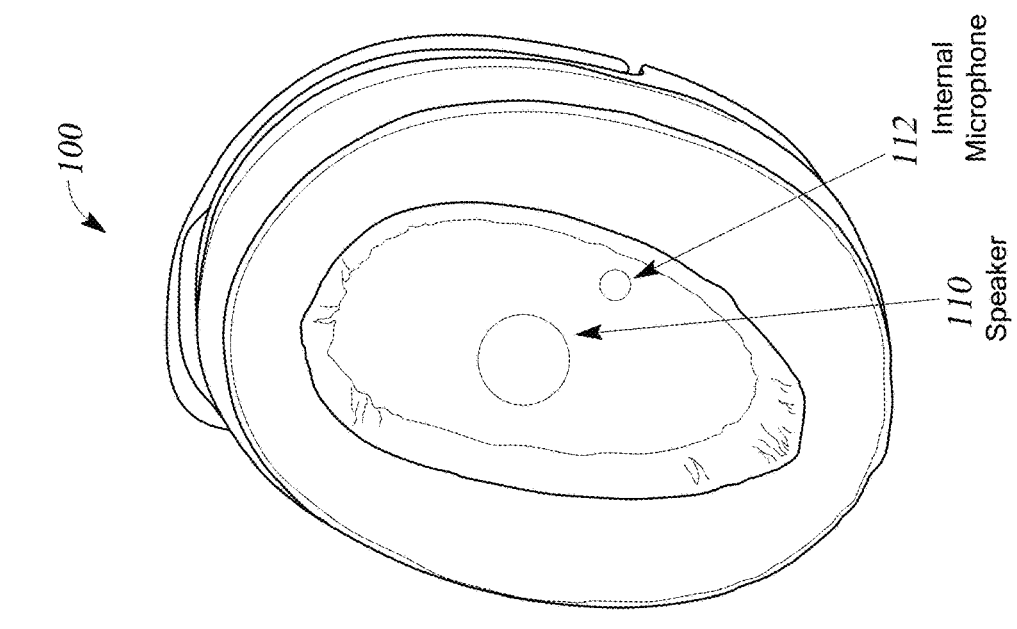
FIGS. 1A-1C illustrate back, side, and front views of one embodiment of a hearing screening device.
Figure 1B:
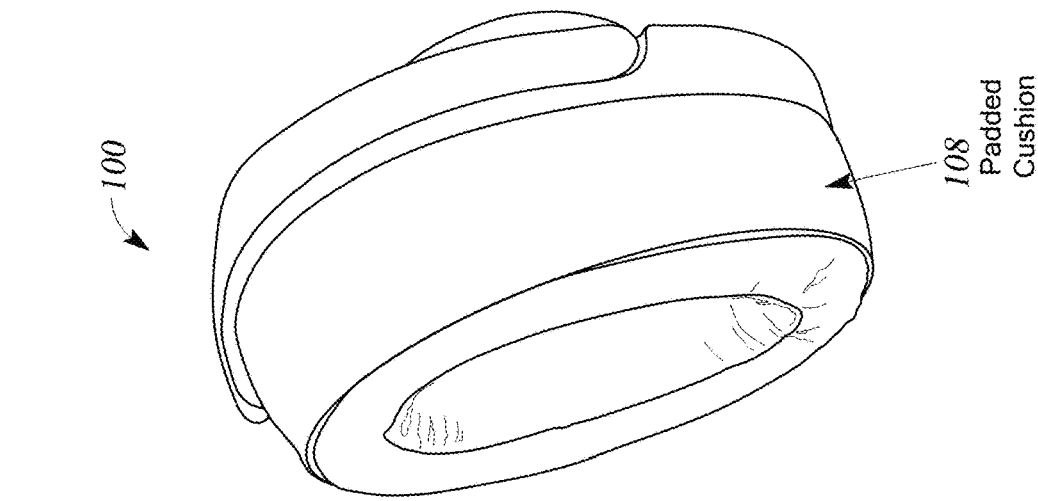
Figure 1A:
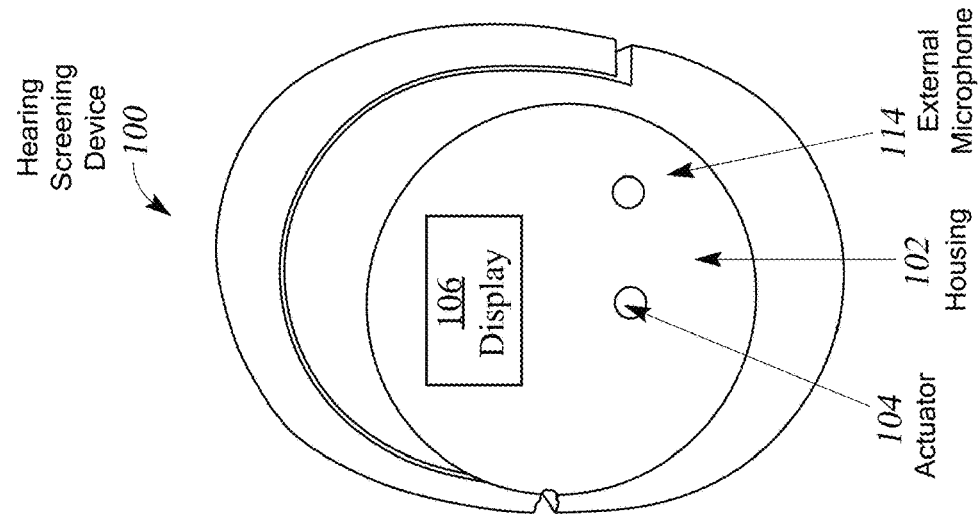

FIGS. 1A-1C illustrate back, side and front views of one embodiment of a hearing screening device 100, which may also be referred to as an auditory function screening device. The hearing screening device 100 includes a housing 102, an actuator 104 and a display 106. The housing 102 encloses various electronic components, including, for example, one or more of the electronic components illustrated in FIG. 2. The housing is sized to be handheld and to fit into the pocket or lab coat of a clinician or medical assistant. The actuator 104 can include a button, switch, or other input to start a hearing screening process, including any of the hearing screening processes described herein. The display 106 may include a liquid crystal display (LCD) and/or light emitting diodes (LEDs) to indicate a number of tones emitted by the hearing screening device 100, as further described below.

A padded cushion 108 of the hearing screening device 100 is sized to surround the outer ear of a user when placed against the side of the user's head. The padded cushion 108 defines an inner cavity that includes a speaker 110 and microphone. The speaker 110 is configured to emit sounds or tones of various frequencies. The frequencies are selected to screen for potential hearing loss in the user. An internal microphone 112 may optionally be included in the inner cavity, an external microphone 114 may optionally be included on the outside of the device, or both internal and external microphones 112, 114 may be provided, to detect ambient noise. In one embodiment, if the device 100 determines that the ambient noise is too loud (e.g., by analyzing the amplitude of the ambient noise detected by one or both of the microphones 112, 114), then the display 106 may present a message or other indication, or an LED may illuminate, to indicate that the padded cushion 108 should be changed to improve the ambient noise reduction within the padded cushion 108. In another embodiment, the device 100 may compare ambient noise levels (e.g., signal amplitudes) of the ambient noise detected by the internal microphone 112 and the external microphone 114. If the ambient noise detected by the internal microphone 112 is not at least a threshold amount less than the ambient noise detected by the external microphone 114, then the device 100 may present a message or indication, e.g., via the display 106 or other indicator, that the test is invalid and/or that the test should be retaken with the padded cushion 108 held closer or tighter to the patient's head.

The hearing screening device 100 is placed against the side of the head of the user such that the padded cushion 108 surrounds one of the user's ears. The actuator 104 is activated and a hearing screening process begins. In one embodiment, the speaker emits a predetermined number of tones of each frequency in a set of test frequencies. The user is instructed to count the tones that the user hears, and to tell the clinician or medical assistant how many tones the user heard. The actual number of generated tones is displayed on the display 106, out of view of the user. The clinician or medical assistant may compare the displayed number of tones to the number of tones actually heard by the user. If the numbers are the same, the clinician may conclude that further auditory function testing is not required. However, if the numbers are different, the clinician may conclude that further auditory function testing is required.

Figure 2:
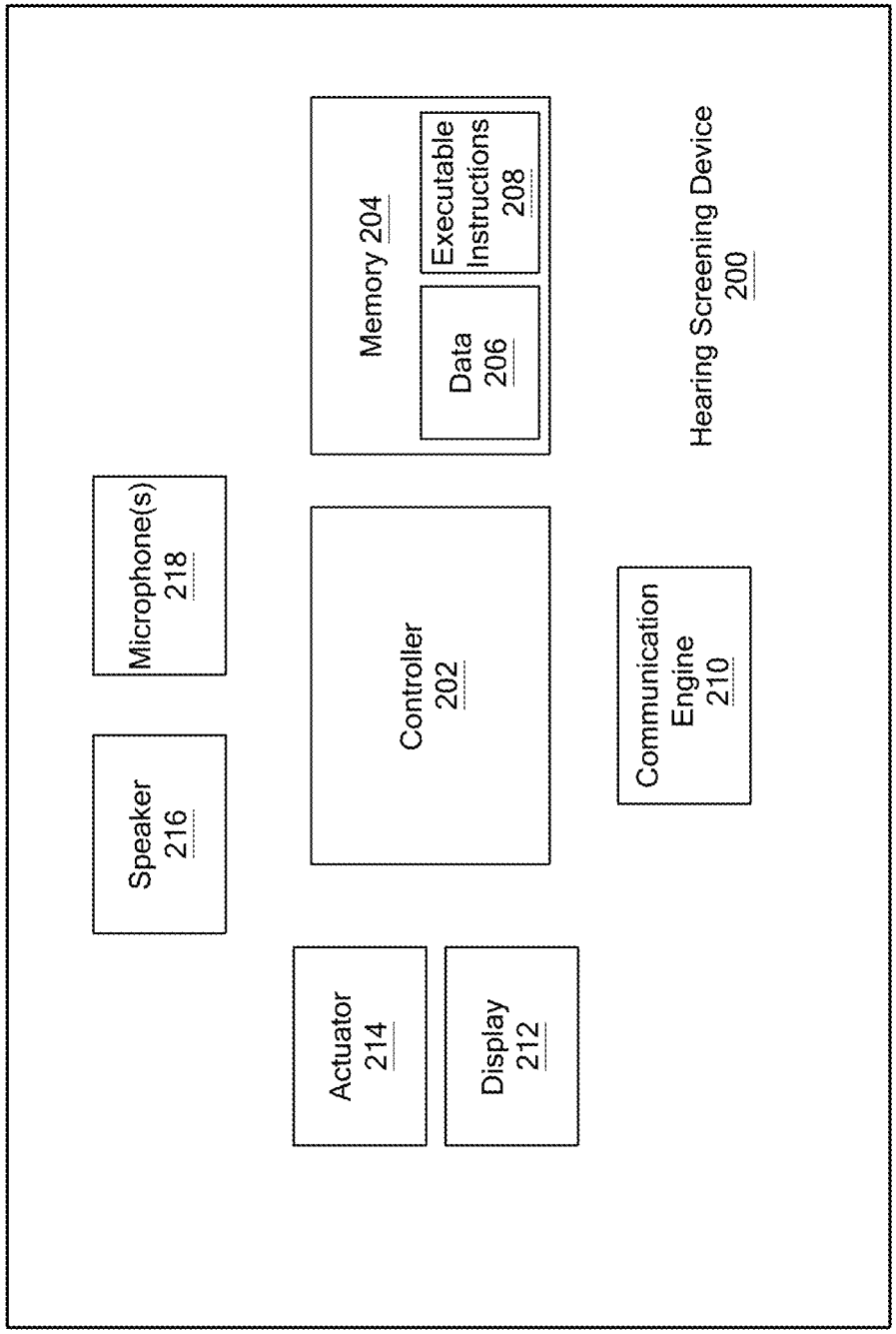
FIG. 2 illustrates a block diagram of components of a hearing screening device, including the hearing screening device of FIGS. 1A-1C.

FIG. 2 illustrates a block diagram of components of a hearing screening device 200, which may include the hearing screening device 100 of FIGS. 1A-1C. The hearing screening device 200 includes a controller 202 that is in communication with a memory 204. The memory 204 stores data 206 and/or executable instructions 208. The data 206 may correspond to the number of times the hearing screening device 200 has been used during a predetermined period of time. The executable instruction 208 may correspond to one or more hearing screening routines, such as the routines described below with respect to FIGS. 4 and 5.

Figure 3:
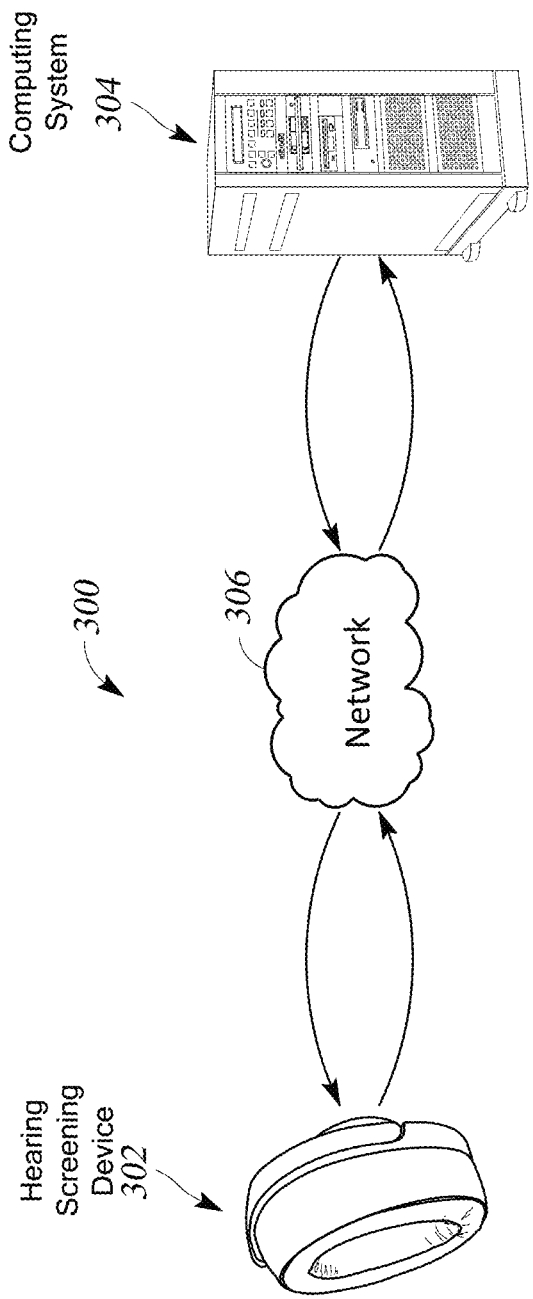
FIG. 3 illustrates a network environment including a hearing screening device and a computing system.

The controller 202 is also in communication with a communication engine 210 that enables wireless communication between the hearing screening device 200 and an external computing device, such as the computing system 304 of FIG. 3. The communication engine 210 may include one or more wireless radios configured to communicate according to an IEEE 802 standard (e.g., 802.11, 802.15, WI-FI®, BLUETOOTH®, etc.).

The controller 202 is also in communication with a display 212, an actuator 214, a speaker 216, and a microphone 218. The display 212 may include an LCD and/or LED(s) to indicate the number of tones emitted by the speaker 216 according to a hearing screening routine. The actuator 214 may include a button, switch, or other user input to initiate, pause, resume, or reset the hearing screening routine. The speaker 216 may emit audible tones according to the hearing screening routine. The microphone(s) 218 (e.g., internal microphone, external microphone, or both) may detect ambient noise that is used by the controller 202 to adjust the amplitude of the tones emitted to the speaker 216 to achieve a desired tone amplitude (e.g., 25 dB). For example, the controller 202 may use the ambient noise to assure that tones are presented to the user at consistent noise levels, such as by determining how much additional gain to provide to present each tone at a constant intensity. The detected ambient noise may also be used by the controller 202 to perform active noise cancellation.

The microphone(s) 218 may also be used to determine if feedback between the speaker 216, microphone 218, and a hearing aid worn by the user during the hearing screening routine is occurring. If the controller 202 determines that feedback is occurring, the controller may terminate the hearing screening routine, and present a message or indication via the display 212 that the hearing screening routine may not be performed.

In other embodiments, a hearing screening device is implemented using a cell phone, tablet, computer, or other portable computing device. For example, the computing device could generate tones according to a hearing screening process and output the tones to a user via a headphone worn by the user. The tones could be directed to only one speaker of the headphone at a time.

Overview of Example Network Environment

FIG. 3 shows a network environment 300 in which aspects of the present disclosure may be implemented for communicating between a hearing screening device 302 and a computing system 304. Devices of the network environment 300 may communicate with a computing system 304 via one or more wired and/or wireless communication networks 306 such as local area networks ("LANs"), virtual local area networks ("VLANs"), wide area networks ("WANs"), the Internet, etc. The network environment 300 may include any number of hearing screening devices 302 and computing systems 304.

The hearing screening device 302 may be any hearing screening device, including, but not limited to, hearing screening device 100 or hearing screening device 200, as described in detail above. The computing system 304 may be any electronic device configured to electronically communicate with other devices over the network 306. In some embodiments, the computing system 304 may be a desktop computer, server computer, network appliance, or the like. The computing system 304 may send or receive data and/or instructions to or from the hearing screening device 302.

The example devices and systems of the network environment shown in FIG. 3 and described herein are illustrative only, and are not intended to be limiting, required, or exhaustive. In some embodiments, the computing system 304 is used to monitor usage of the hearing screening device 302. Each time the hearing screening device 302 is used, it sends a message to the computing system 304 to indicate that the hearing screening device 302 has been used.

The computing system 304 may be configured to monitor hearing screening device 302 usage, and to take corrective action if it determines that usage does not meet predetermined thresholds. For example, if the computing system 304 determines that the fewer than a predetermined number of uses occur within a predetermined time period, the computing system 304 may automatically generate and send a notification of non-use and provide instructions, or offer assistance or training to facilitate increased usage.

One embodiment of a method of non-use remediation is described below with respect to FIG. 6

Hearing Screening Processes

Figure 4:
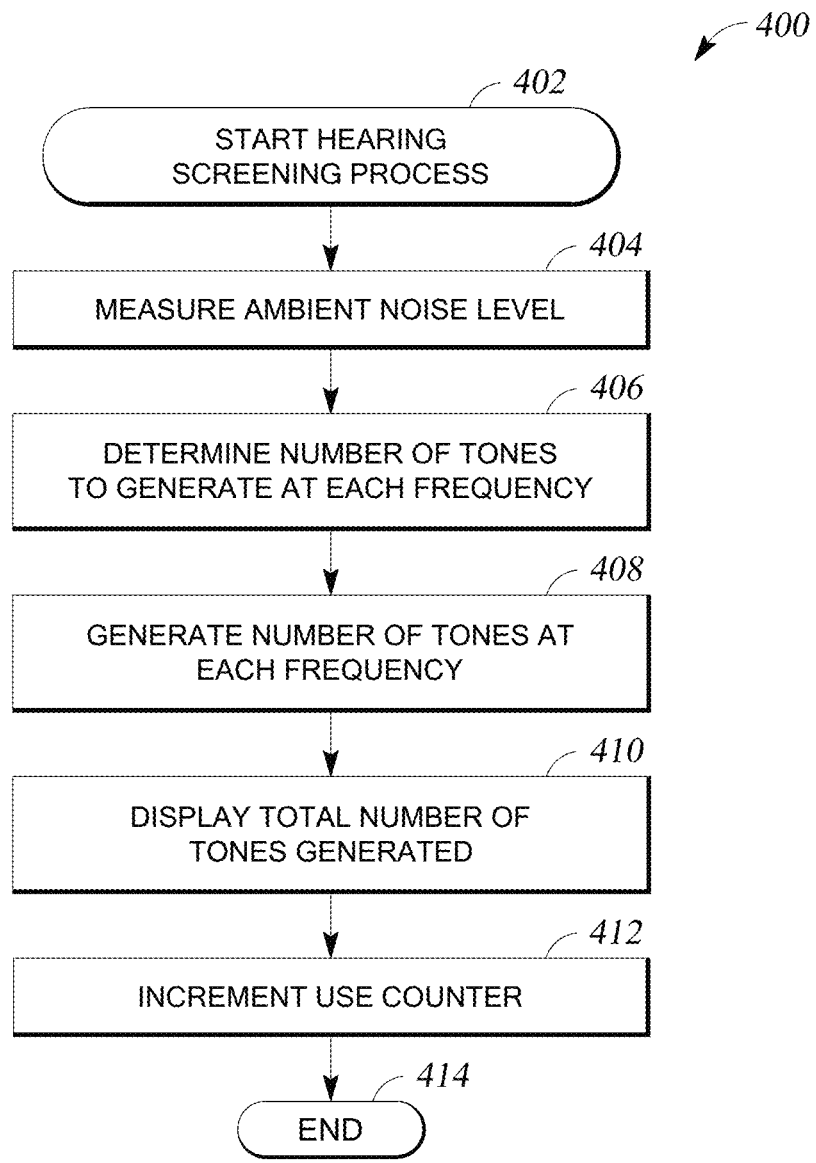
FIG. 4 illustrates a flow chart of a hearing screening process that may be implemented by a hearing screening device, including the hearing screening devices of FIGS. 1A-1C, 2 and 3.

FIG. 4 is a flow diagram of an illustrative hearing screening process routine 400 that may be implemented by any of the hearing screening devices described herein, including hearing screening devices 100, 200, and 302. The routine 400 begins at block 402. At block 404, ambient noise is measured. For example, a microphone of a hearing screening device may detect ambient noise, and circuitry of the hearing screening device may determine an ambient noise amplitude level from the detected ambient noise.

At block 406, the routine 400 determines a number of tones to generate at each frequency of a set of frequencies. For example, the routine 400 may determine to generate one, two, three, or more tones at each frequency of a set of frequencies. The set of frequencies may include five different frequency values, e.g., 500 Hz, 1000 Hz, 2000 Hz, 4000 Hz, and 6000 Hz. The routine 400 may determine the number of tones to generate by randomly selecting an integer value within a predetermined range (e.g., 1 to 5, 2 to 4, 1 to 3, etc.). Alternatively, the routine 400 may determine the number of tones to generate by receiving a selection from a user, e.g., via a user input, button press, etc.

At block 408, the routine 400 generates the number of tones at each frequency of the set of frequencies. For example, if the number of tones to generate is determined to be 2, and the set of frequencies includes 5 different frequencies, then the routine 400 will generate a total of 10 tones—two at each of the five frequencies. Generating the tone includes causing a speaker of the hearing screening device to emit a sound at the current frequency and at a predetermined amplitude. For example, the sound may be emitted at 25 dB above the ambient noise level detected by the hearing screening device's microphone. For example, the amplitude, or sound intensity of the emitted tone, may be determined using the relationship $dB = 10 \times \log(I/I_{ambient})$, or $I = I_{ambient} \times 10^{dB/10}$. The dB level may be any gain level described herein, including but not limited to 20, 22, 25, 27, 30, 35 dB, or any user selectable value. In another embodiment, the routine 400 generates a random number of tones for each frequency. The random number may be any integer number, such as 1, 2, or 3. For example, the routine 400 may determine that 3 tones will be generated at a first frequency, 2 tones at a second frequency, 3 tones at a third frequency, 1 tone at a fourth frequency, etc.

At block 410, the routine 400 displays the total number of tones generated. For example, if the number of tones to generate is determined to be 2, and the set of frequencies includes 5 different frequencies, then an indication that 10 tones have been generated will be displayed. The total number (e.g., 10) may be displayed on a screen (e.g., an LCD screen), or an LED corresponding to 10 tones may be illuminated.

At block 412, the routine 400 increments a use counter. For example, a use value stored in the hearing screening device may be incremented by one. In another embodiment, a message indicating that the hearing screening device has been used is sent to a computing device, such as the computing system 304 of FIG. 3.

At block 414, the routine 400 ends.

Figure 5:
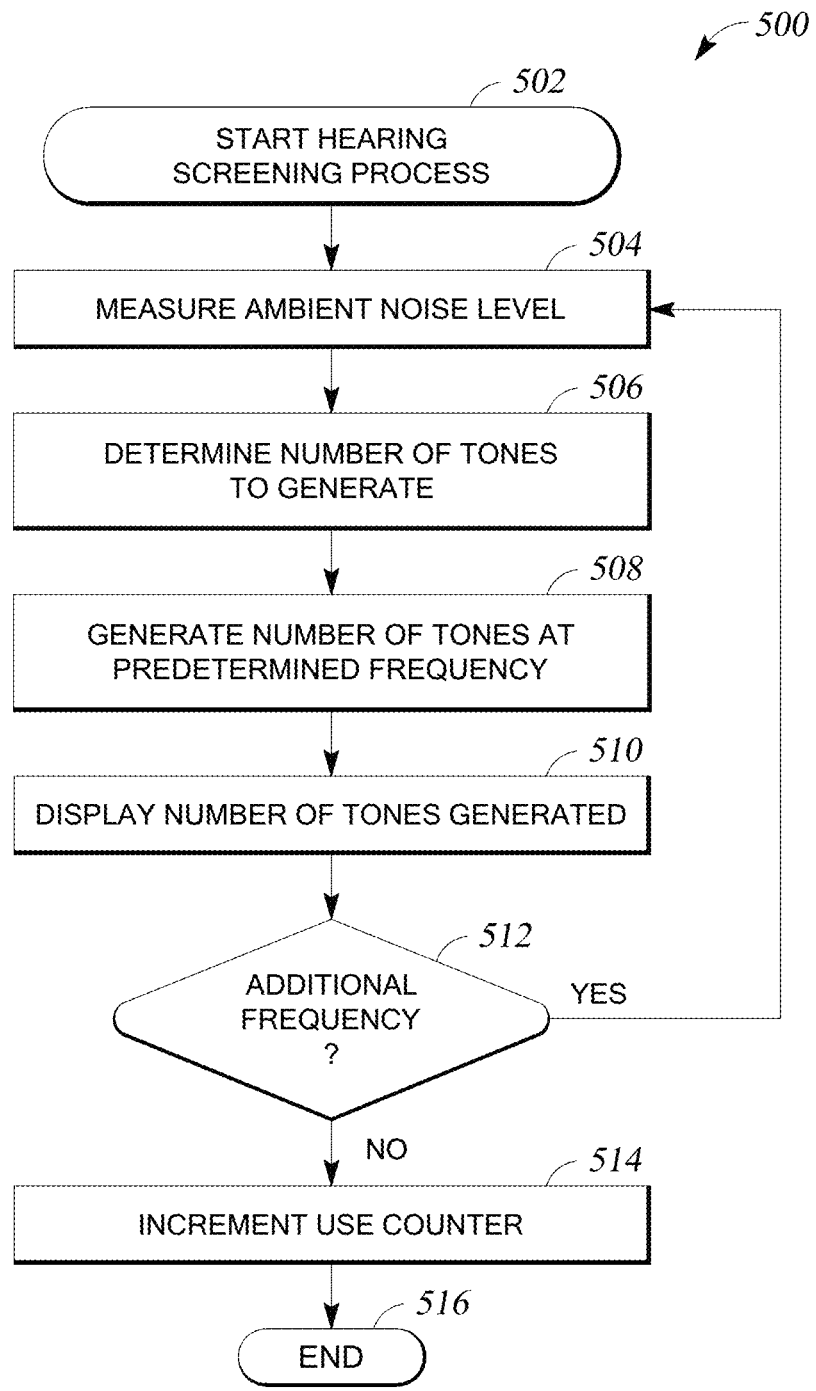
FIG. 5 illustrates a flow chart of another hearing screening process that may be implemented by a hearing screening device, including the hearing screening devices of FIGS. 1A-1C, 2 and 3.

FIG. 5 is a flow diagram of an illustrative hearing screening routine 500 that may be implemented by any of the hearing screening devices described herein, including hearing screening devices 100, 200, and 302. The routine 500 begins at block 502. At block 504, ambient noise is measured. For example, a microphone of a hearing screening device may detect ambient noise, and circuitry of the hearing screening device may determine an ambient noise amplitude level from the detected ambient noise.

At block 506, the routine 500 determines a number of tones to generate. The number of tones to generate is specific to each frequency of a set of frequencies, and may be different for different frequencies. For example, the routine 500 may determine to generate one tone at the first frequency of the set of frequencies, two tones at the second frequency of the set of frequencies, two tones at the third frequency of the set of frequencies, one tone at the fourth frequency of the set of frequencies, and three tones at the fifth frequency of the set of frequencies. In some embodiments, at least two numbers of tones are different from each other. The set of frequencies may include five different frequency values, e.g., 500 Hz, 1000 Hz, 2000 Hz, 4000 Hz, and 6000 Hz. The routine 500 may determine the number of tones specific for each frequency by randomly selecting an integer value within a predetermined range (e.g., 1 to 5, 2 to 4, 1 to 3, etc.). Alternatively, the routine 500 may determine the number of tones to generate by receiving a selection from a user, e.g., via a user input, button press, etc.

At block 508, the routine 500 generates the number of tones at the current frequency of the set of frequencies. For example, if the numbers of tones to generate at the first frequency is determined to be 1 then the routine 500 will generate one tone at the first frequency the first time the process 500 reaches block 508. Generating the tone includes causing a speaker of the hearing screening device to emit a sound at the current frequency and at a predetermined amplitude. For example, the sound may be emitted at 25 dB above the ambient noise level detected by the hearing screening device's microphone. For example, the amplitude, or sound intensity of the emitted tone, may be determined using the relationship $dB = 10 \times \log(I/I_{ambient})$, or $I = I_{ambient} \times 10^{dB/10}$. The dB level may be any gain level described herein, including but not limited to 20, 22, 25, 27, 30, 35 dB, or any user selectable value.

At block 510, the routine 500 displays the number of tones generated at the current frequency. For example, if the numbers of tones to generate is determined to be 1 for the first frequency, then an indication that 1 tone have been generated will be displayed. The total number (e.g., 9) may be displayed on a screen (e.g., an LCD screen), or an LED corresponding to 9 tones may be illuminated.

At block 512, the routine 500 determines if there are any additional frequencies in the set of frequencies that need to be emitted from the speaker as part of the hearing screening process. For example, if the set of frequencies includes five different frequencies, and only tone(s) of the first frequency have been generated, the next frequency of the set of frequencies (e.g., the second frequency) will be selected and the routine 500 will return to block 504. Block 506, 508 and 510 will be repeated, but this time using the second frequency, determining a number of tones of the second frequency to generate, generating the second frequency tones, and displaying the number of tones generated. In another embodiment, the routine 500 displays the number of tones generated immediately before proceeding to block 514, instead of before proceeding to block 512. In such embodiment, all tones of all frequencies are generated and presented to the patient, and the patient is instructed to count the total number of tones that were heard. The clinician may then compare the total number of heard tones to the total number of displayed tones to determine if there is a difference. If so, the clinician may determine that the user may be experiencing some hearing loss, such as at one or more of the generated frequencies. For example, the routine 500 may generate a randomly selected number or predetermined number of tones at each testing frequency and display the total number of generated tones after all tones at all frequencies are generated. If the routine 500, for example, generates two tones at 500 Hz, two tones at 1 kHz, 3 tones at 2 kHz, two tones at 4 kHz, and two tones at 6 kHz, the routine will display that 11 tones have been generated. If the patient indicates that she heard any number other than 11 tones, then the clinician may determine that the patient may be experiencing some hearing loss.

At block 514, the routine 500 increments a use counter. For example, a use value stored in the hearing screening device may be incremented by one. In another embodiment, a message indicating that the hearing screening device has been used is sent to a computing device, such as the computing system 304 of FIG. 3.

At block 514, the routine 500 ends.

In other embodiments, a hearing screening routine presents one or more of a Quick SIN (signal in noise) test, a HINT (hearing in noise) test, or a Sentence in Noise test (such as the AzBio Sentence Test). The AzBio Sentence in Noise test, or AzBio test, involves presenting a user with a variety of pre-recorded sentences from male and female talkers and determining whether the recorded sentence is understood by a subject.

Hearing Screening Non-Use Remediation

Figure 6:
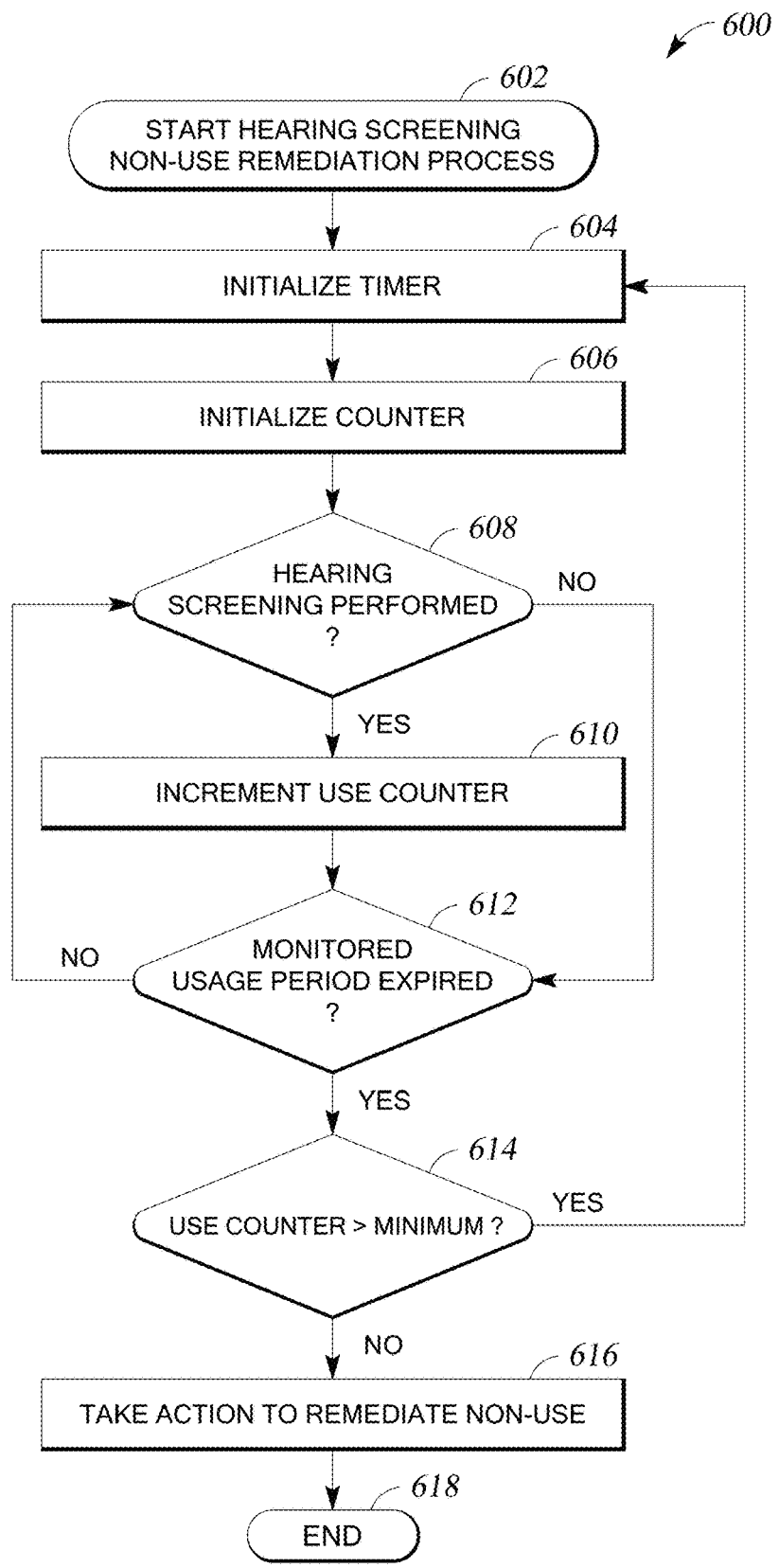
FIG. 6 illustrates a flow chart of a hearing screening non-use remediation process that may be implemented by a computing system, including the computing system of FIG. 3.

FIG. 6 is a flow chart of an illustrative routine 600 for hearing screening non-use remediation. The routine 600 begins at block 602. At block 604 a timer is initialized. For example, a memory stores an indication of the current time, or a start time of a monitored usage period, or a timer is reset and then started. The monitored usage period can be any predetermined period, such as a day, a week, two weeks, a month, two months, three months, six months, a year, or other period.

At block 606 a counter is initialized. For example, a use value stored in a memory location may be set to zero, indicating that no uses of a hearing screening device have occurred during the monitored period, so far. At block 608, the routine 600 determines whether a hearing screening process has been performed. For example, the routine 600 may receive an indication from a hearing screening device that a hearing screening process has occurred.

If a hearing screening process has been performed, the routine 600 proceeds to block 610; if not, the routine 600 proceeds to block 612. At block 610 the use counter is incremented. For example, the stored use value may be increased by one. At block 612, the routine 600 determines whether the monitored usage period has expired. For example, the routine 600 may calculate the difference between the current time and the initialized time, or determine if the timer has reached the monitored usage period. If the monitored usage period has not expired, the routine 600 returns to block 608. If the monitored usage period has expired, the routine 600 proceeds to block 614.

At block 614, the routine 600 determines whether the use counter value is greater than a predetermined minimum number of uses for the monitored usage period. For example, the routine 600 may determine if hearing screening has been performed at least 10, 20, 30, 40, 50 or more or fewer times during the previous 24-hour period. If the use counter value is greater than the predetermined minimum number of uses, the routine 600 returns to block 604; otherwise, the routine 600 continues to block 616.

At block 616, the routine 600 takes an action to remediate non-use. For example, the routine 600 may send a message, for example, to the clinician's office or to the equipment supplier, or a third party, to indicate that the usage of the hearing screening device has not occurred more than the minimum number of times for the given monitored period. The routine 600 may also provide additional training information or contact information for the recipient to use to acquire additional training regarding hearing screening device usage.

At block 618, the routine 600 ends.

OTHER CONSIDERATIONS

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a computer processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A computer processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a", "an", or "the" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be implemented within a form that does not provide all of the features and benefits set forth herein, as some features can be used or practiced separately from others. All such modifications and variations are intended to be included herein within the scope of this disclosure. Further, additional embodiments created by combining any two or more features or techniques of one or more embodiments described herein are also intended to be included herein within the scope of this disclosure.

What is claimed is:

1. An auditory function screening device configured to screen a user for possible hearing loss, comprising:
    a controller;
    a speaker coupled to the controller and configured to generate tones of each frequency of a set of test frequencies;
    a microphone coupled to the controller and configured to detect ambient noise;
    an actuator, coupled to the controller and configured to be activated to initiate an auditory function screening test;
    a display coupled to the controller and configured to display an indication corresponding to a total number of generated tones; and
    a memory coupled to the controller, the memory storing executable instructions that when executed by the controller cause the auditory function screening device to perform the auditory function screening test, the auditory function screening test comprising:
        detecting an ambient noise amplitude from the ambient noise;
        determining a gain adjustment based on the detected ambient noise amplitude;
        generating a predetermined number of tones of each frequency of the set of test frequencies at a predetermined gain level based on the gain adjustment;
        presenting an indication corresponding to the total number of generated tones; and
        causing a use counter to be incremented, wherein the use counter indicates a number of times that the auditory function screening device has been used during a monitored usage period, wherein causing the use counter to be incremented comprises sending a message to an external computing device.

2. The auditory function screening device of claim 1, wherein the controller comprises a microprocessor or a microcontroller.

3. The auditory function screening device of claim 1, wherein the display comprises a screen or a light emitting diode.

4. The auditory function screening device of claim 1, further comprising a radio configured to communicate according to an IEEE 802 wireless networking standard.

5. The auditory function screening device of claim 1, wherein the memory is further configured to store data corresponding to the use counter.

6. The auditory function screening device of claim 1, wherein the auditory function screening test comprises determining the gain adjustment such that the auditory function screening test generates the tones at a gain of 25 dB above the ambient noise amplitude.

7. The auditory function screening device of claim 1, wherein the set of test frequencies includes 500 Hz, 1000 Hz, 2000 Hz, 4000 Hz, and 6000 Hz.

8. The auditory function screening device of claim 1, wherein the auditory function screening test comprises causing the use counter to be incremented by retrieving a use counter value from the memory, increasing the use counter value by one, and storing the increased use counter value in the memory.

9. The auditory function screening device of claim 1, wherein the auditory function screening test comprises causing the use counter to be incremented by proving an indication to a remote computing system that the auditory function screening test has been performed.

10. The auditory function screening device of claim 1, wherein the controller is further configured to perform active noise cancellation using the detected ambient noise.

11. The auditory function screening device of claim 1, wherein the predetermined number of tones is the same for each frequency of the set of test frequencies.

12. The auditory function screening device of claim 1, wherein the predetermined number of tones is different for at least two frequencies of the set of test frequencies.

13. The auditory function screening device of claim 1, wherein the monitored usage period is a day, a week, two weeks, a month, two months, three months, six months, or a year.

14. A method of performing auditory function screening to screen a user for possible hearing loss, comprising:
    determining an ambient noise amplitude;
    determining a gain adjustment based on the determined ambient noise amplitude;
    generating a predetermined number of tones of each frequency of a set of test frequencies at a predetermined gain level based on the gain adjustment;
    presenting an indication corresponding to the predetermined number of tones; and
    causing a use counter to be incremented, wherein the use counter indicates a number of times that the auditory function screening device has been used during a monitored usage period, wherein causing the use counter to be incremented comprises sending a message to an external computing device.

15. The method of claim 14, further comprising communicating with an external computing device according to an IEEE 802 wireless networking standard.

16. The method of claim 14, further comprising storing data corresponding to the use counter.

17. The method of claim 14, further comprising determining the gain adjustment such that the tones are generated at a gain of 25 dB above the determined ambient noise amplitude.

18. The method of claim 14, wherein the set of test frequencies includes 500 Hz, 1000 Hz, 2000 Hz, 4000 Hz, and 6000 Hz.

19. The method of claim 14, further comprising causing the use counter to be incremented by retrieving a use counter value from a memory, increasing the use counter value by one, and storing the increased use counter value in the memory.

20. The method of claim 14, further comprising causing the use counter to be incremented by proving an indication to a remote computing system that the auditory function screening test has been performed.

21. The method of claim 14, further comprising detecting ambient noise and performing active noise cancellation using the detected ambient noise.

22. The method of claim 14, wherein the predetermined number of tones is the same for each frequency of the set of test frequencies.

23. The method of claim 14, wherein the predetermined number of tones is different for at least two frequencies of the set of test frequencies.

24. The method of claim 14, wherein the monitored usage period is a day, a week, two weeks, a month, two months, three months, six months, or a year.

* * * * *